United States Patent [19]

Thompson et al.

[11] Patent Number: 4,596,374
[45] Date of Patent: Jun. 24, 1986

[54] CLAMP VALVE

[75] Inventors: John U. Thompson, Tinley Park; David M. Bergemann, Vernon Hills, both of Ill.

[73] Assignee: Baxter Travenol Laboratories, Inc., Deerfield, Ill.

[21] Appl. No.: 676,131

[22] Filed: Nov. 29, 1984

[51] Int. Cl.$^4$ ............................................. F16L 55/14
[52] U.S. Cl. ......................................... 251/7; 251/8; 251/129.11
[58] Field of Search .................. 251/7, 8, 133, 337

[56] References Cited

U.S. PATENT DOCUMENTS

| | | | |
|---|---|---|---|
| 2,219,201 | 10/1940 | Smith | 137/355.23 |
| 2,614,788 | 10/1952 | Woodward | 251/5 |
| 2,663,318 | 12/1953 | Lakso | 137/641 |
| 2,673,011 | 3/1954 | Rood et al. | 222/207 |
| 3,042,357 | 7/1962 | Engholdt | 251/133 |
| 3,080,952 | 3/1963 | Carlstedt | 251/133 |
| 3,248,080 | 4/1966 | Plasko | 222/63 |
| 3,505,888 | 4/1970 | Denkowski | 251/133 |
| 3,601,124 | 8/1971 | Petree | 251/8 |
| 3,749,098 | 7/1973 | DeBennetot | 251/133 |
| 4,099,700 | 7/1978 | Young | 251/133 |
| 4,106,508 | 8/1978 | Berlin | 251/7 |
| 4,203,573 | 5/1980 | Boss | 251/249.5 |
| 4,239,179 | 12/1980 | Geier | 251/133 |
| 4,397,642 | 8/1983 | Lamadrid | 251/9 |
| 4,500,478 | 2/1985 | Furukawa et al. | 251/133 |

Primary Examiner—Martin P. Schwadron
Assistant Examiner—Sheri M. Novack
Attorney, Agent, or Firm—Paul C. Flattery; Kay H. Pierce; Paul M. Vargo

[57] ABSTRACT

An occluder valve for closing off the flow of fluid in a flexible plastic tube includes a linearly movable pinch member coupled to a rotatable shaft through a nut. The shaft is coupled to an electric motor through an electrically energizable clutch. The output shaft of the motor is mechanically constrained to rotate in only one direction. The motor, coupled through the clutch, rotates the shaft causing the pinch member to move linearly away from the tubing. A torsion spring opposes this rotation. Once opened the valve will stay opened as long as the clutch is energized as the shaft of the motor will not rotate in a closing direction. To close the valve, the clutch is deenergized and the torsion spring moves the pinch member linearly against the flexible tubing closing it off.

1 Claim, 7 Drawing Figures

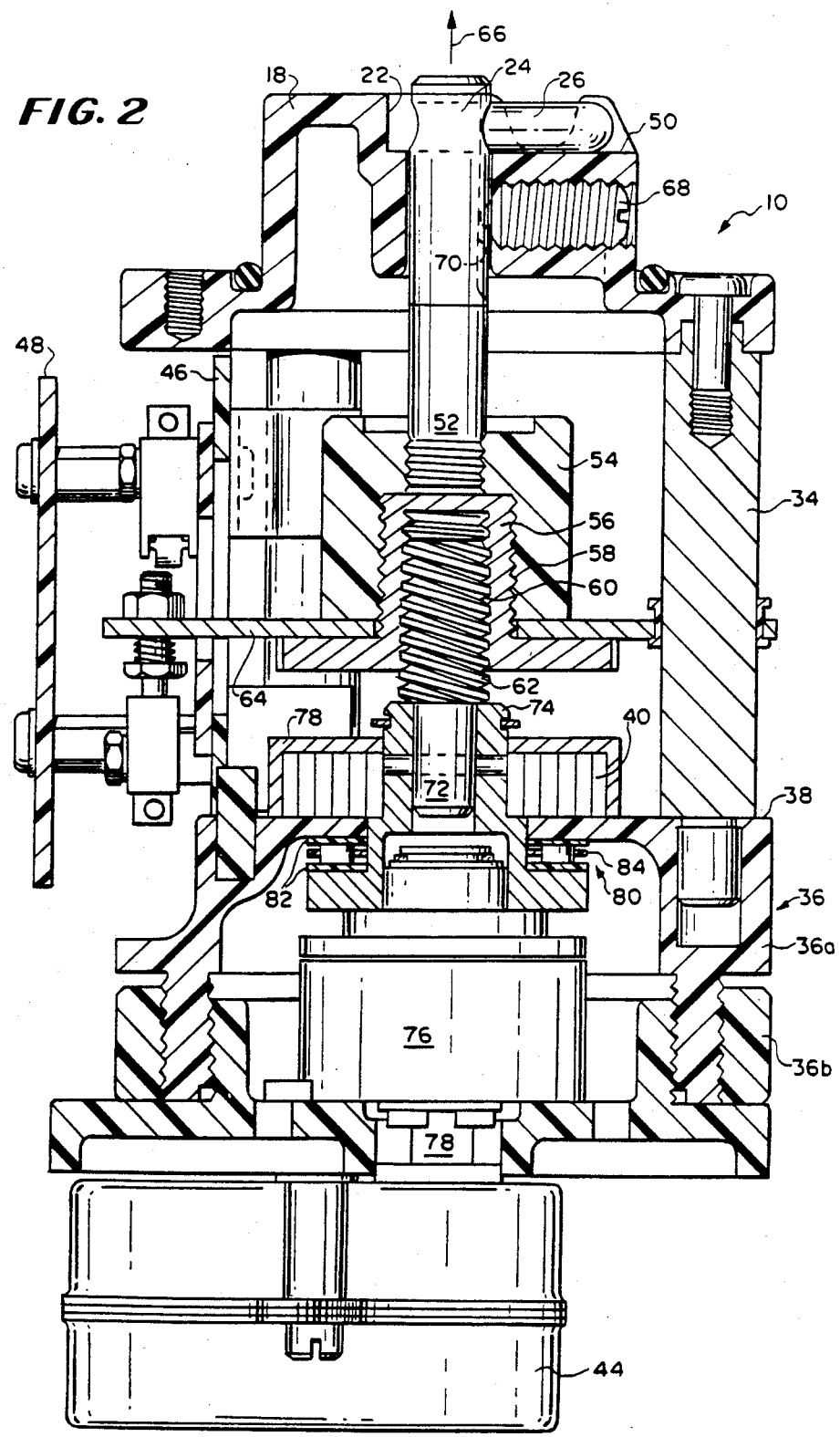

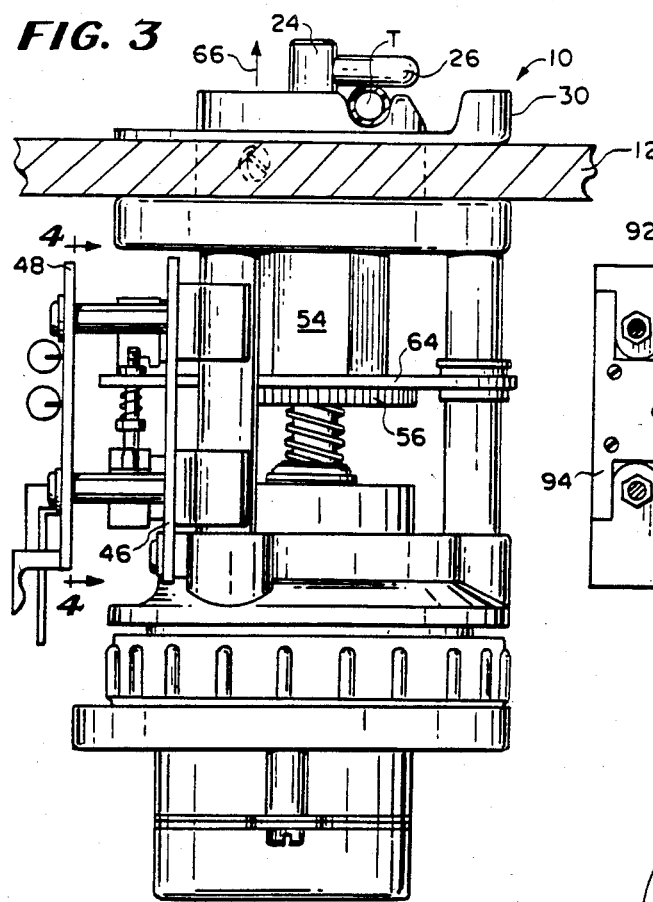
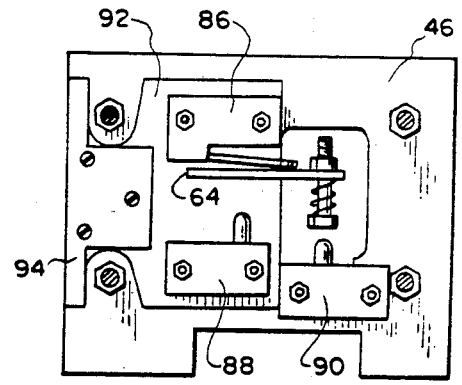
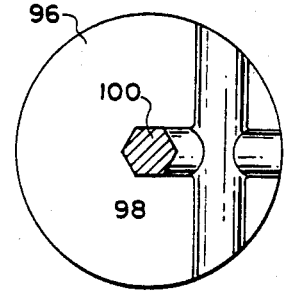
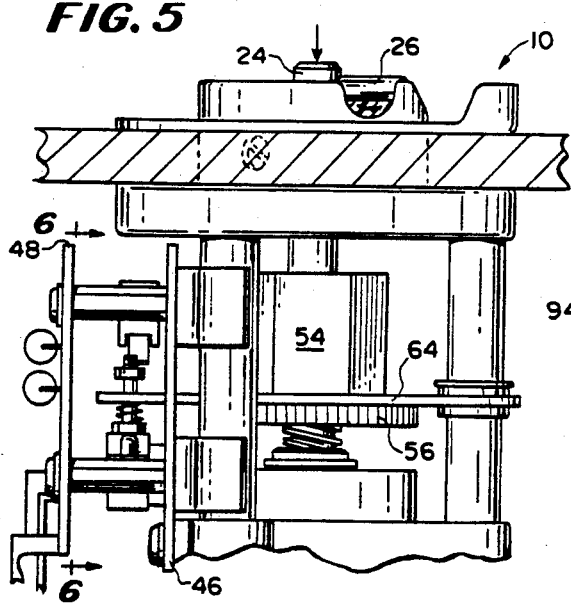
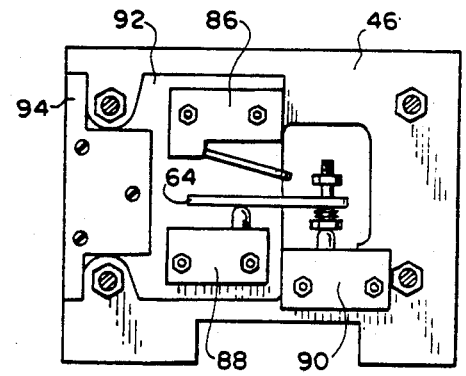

CLAMP VALVE

FIELD OF THE INVENTION

The invention pertains to occlusion controllers or valves for closing off a flexible conduit through which fluid flows.

BACKGROUND OF THE INVENTION

Peritoneal dialysis systems provide for the cycling of dialysis fluids through a patient's peritoneum. The cycling process includes pumping fresh fluid into the peritoneal cavity as well as removing spent fluid after a predetermined time interval. Electrically controllable valves which will reliably open and close paths for the fluid flow are often needed in such dialysis systems.

In view of the fact that patient treatment is involved, the fluids involved are sterile and the occlusion devices or valves must not come in contact with the fluid. Separation of the valve mechanism from the fluid is conventionally accomplished by using flexible sterile tubing through which the fluid can be permitted to flow or be pumped and which can be pinched closed by an appropriate apparatus. Such an apparatus is disclosed in U.S. Pat. No. 4,397,642 entitled "Motor Driven Occlusion Controller For Liquid infusion And The Like." The occlusion apparatus disclosed in this patent incorporates a stepping motor in combination with a clamping member which moves in a curvilinear direction under the control of the stepping motor to unclamp a tube through which fluid is to flow. This occluder valve is designed to automatically close subsequently by means of a spring member thereby pinching the tubing closed.

Alternately, solenoid actuators could be used to provide an electrically controllable valve, which can be opened in response to an applied electrical signal and which will close due to spring loading upon removal of the electrical signal.

SUMMARY OF THE INVENTION

The present invention provides an efficient electrically operated, high speed tubing clamp or occluder valve for controlling the flow of fluid through a flexible tube inserted into the valve. An embodiment of the present invention includes a supporting member, means affixed to the supporting member for receiving a tube to be clamped, means for converting a selected electrical signal to continuous mechanical movement in a first direction, transferring means coupled to the converting means for transferring the continuous mechanical movement in the first direction to linear movement and means for clamping the tube against the receiving means in response to linear movement from the transferring means.

A further embodiment of the invention includes an electrical motor with an output shaft rotatable only in one direction in response to an applied electrical signal, an electrically actuatable clutch coupled to the output shaft of the motor, a threaded shaft coupled to an output of the electrically actuatable clutch and a clamping member threadably connected to the threaded shaft along with a torsion spring connected to the threaded shaft.

As the output shaft of the motor rotates in the first direction, if the electrical clutch is energized, the shaft is rotated winding the torsion spring and linearly moving the clamping member coupled to the shaft away from the tubing to be closed. After the clamping member has been moved away from the tubing, thereby permitting the flow of fluid therethrough, the electrical motor may be deenergized. Since the output shaft of the motor is mechanically able to rotate in only a first, opening, direction, the torsion spring is unable to move the clamping member against the tubing so long as the electrical clutch is energized. Once the electrical clutch has been deenergized the torsion spring rotates the shaft in the opposite direction causing the clamping member to linearly move against the tubing thereby shutting off the flow of fluid.

The present invention produces a surprising result in that substantial closing forces are generated by the clamping member on the tubing due to the mechanical advantage realized between the torsion spring and the threaded shaft coupled thereto. These forces, on the order of 20 pounds, substantially exceed the forces generatable directly by the torsion spring or by the energizing motor. As a result, the tubing is closed immediately with a force much greater than would be expected merely from the size of the spring alone.

Additionally the present invention, is surprisingly energy efficient. The motor is only actuated during a short time interval during which the clamping member is being moved linearly away from the tube. Once the valve is opened and fluid starts flowing through the tube the motor is deenergized and only the electrical clutch, which consumes approximately one half of the total power of the unit, need be energized to maintain the valve in its open position. Finally, the present invention is advantageous in that when the electrical clutch is deenergized the magnitude of the closing forces exerted by the closing member is such that the tube is closed off essentially immediately.

BRIEF DESCRIPTION OF THE DRAWINGS

FIG. 2 is a sectional view of the valve of FIG. 1 taken generally along a center line of the valve.

FIG. 3 is a side view of the valve of the present invention illustrating the mechanical relationships among the elements of the valve when the valve is open.

FIG. 4 is a planar view taken along line 4—4 of FIG. 3 illustrating a switch assembly and the conditions thereof when the valve is open.

FIG. 5 is a fragmentary side view of the valve embodying the present invention illustrating the mechanical relationships between the elements of the valve when the valve is closed.

FIG. 6 is a planar view taken along line 6—6 of FIG. 5 of the switch assembly and the conditions thereof when the valve is closed.

FIG. 7 is a planar partial view of an alternate embodiment of the present invention.

DETAILED DESCRIPTION OF THE PREFERRED EMBODIMENTS

Figure 1:
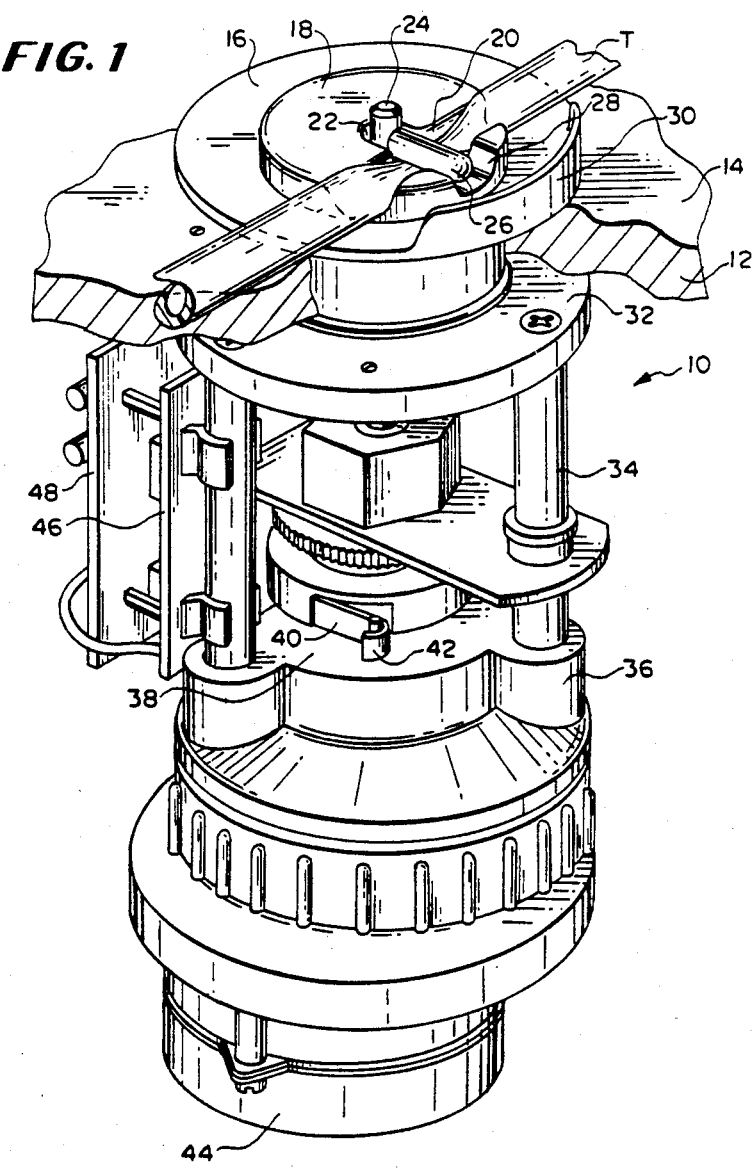
FIG. 1 is perspective view of a valve embodying the present invention.

With respect to the figures, FIG. 1 illustrates a clamp valve 10 embodying the present invention. The valve 10 is mounted on a panel 12 which is partly broken away in FIG. 1. The panel 12 has a top surface 14 on which is positioned a bezel 16 of the valve 10. The bezel 16 encircles an upper head support assembly 18 with a cylindrical slot 20 formed therein for the purpose of receiving a piece of flexible tubing T. The tubing T provides a conduit for various fluids the flow of which is to be controlled by the clamp valve 10.

Extending through a centered hole 22 in the head support assembly 18 is a linearly movable clamp bar assembly 24. The assembly 24 is linearly movable from a clamping position as illustrated in FIG. 1 to an unclamping position as discussed below. The assembly 24 has affixed thereto, at essentially a 90 degree angle, a tubing clamping bar 26 whose purpose is to pinch off a section of the tubing T when the assembly 24 has been moved linearly downwardly with respect to the valve 10 to the clamping position of FIG. 1.

The clamping bar 26 is oriented to drop into a slot 28 also formed in the head support assembly 18. Adjacent the slot 28 is a raised portion 30 of the bezel 16. The orientation of the raised portion 30 of the bezel 16, adjacent the slot 28 is for the purpose of minimizing the likelihood of a person inserting a finger under the clamping bar 26 and becoming injured when the assembly 24 moves linearly into the valve 10 for the purpose of clamping the tubing T.

Further with respect to FIG. 1, the head support assembly 18 of the valve 10 is supported under the panel 12 by a cylindrical disk 32. The cylindrical disk 32 is in turn supported by three spaced apart support rods 34. The support rods 34 are each in turn supported by a clamp base assembly 36. An upper surface 38 of the clamp base assembly 36 supports a torsion spring 40 and anchors an end 42 of the torsion spring 40. An electric motor 44 is affixed to the bottom of the clamp base assembly 36. A control switch assembly 46 is removably attached to a pair of the support rods 34. The control switch assembly 46 in turn carries a drive select assembly 48.

FIG. 2, a sectional view of the valve 10 illustrates in section the head support assembly 18 and the clamp bar assembly 24 with no tubing inserted into the slot 20. In this condition, as shown in FIG. 2, the clamp bar assembly 24 has moved linearly downwardly into the valve 10 moving the clamping bar 26 against a lower surface 50 of the slot 28. The clamp bar assembly 24 is formed as a cylindrical shaft and has a lower threaded end 52 which threadably engages a plastic retaining nut 54. The lower end 52 of the clamp bar assembly 24 could for example be a 5/16"-18 screw. The plastic retaining nut 54 in turn threadably engages a clamp nut 56 which has an exterior set of threads 58, used to engage the nut 54 and an interior set of threads 60. The interior set of threads 60 is used to engage the threads of a screw 62, for example a ⅜"-12 acme screw. Between the retaining nut 54 and the clamp nut 56 is positioned a switch actuator assembly 64. The actuator assembly 64 is carried by and moves in unison with the threadably engaged nuts 54, 56.

As the screw 62 is rotated in a first direction, the clamp bar assembly 24 moves in an unclamping, linear, direction indicated by an arrow 66 lifting the clamping bar 26 out of the slot 28 to the unclamping position. The clamp bar assembly 24 is constrained to move only linearly by a plurality of spring loaded ball plungers 68 which are spaced about the cylindrical clamp bar assembly 24. Each plunger 68 engages a selected surface 70 formed on the shaft of the assembly 24.

When the screw 62 rotates in the opposite direction the clamp bar assembly 24 moves linearly in a clamping direction, opposite the direction of the arrow 66, so as to bring the clamping bar 26 toward and into contact with the tubing T positioned in the slot 20. As the screw 62 is rotated, the interlocking nuts 54, 56 move linearly along with the clamp bar assembly 24. Similarly, the switch actuator assembly 64 moves in unison with the interlocked nuts 54, 56.

A lower end 72 of the screw 62 is pinned to a hub 74 of an electrically engageable clutch 76. Output shaft 78 from the motor 44 provides continuous rotary input, in a first direction, to an input port to the electrically engageable clutch 76. When the clutch 76 is engaged by having a selected electrical signal applied thereto the hub 74 rotates which in turn causes the screw 62 to rotate so as to move the assembly 24 in the unclamping direction 66.

Positioned on the surface 38 of the clamp base assembly 36, as can be seen from FIG. 2, is the torsion spring 40. The torsion spring 40 is covered by a cover 79. As can be seen with respect to FIG. 1, one end of the torsion spring 40 is anchored to the housing 36. The other end of the torsion spring 40 engages a slot in the clutch hub 74. The output shaft 78 of the motor 44 is constrained to rotate only in a first selected direction by a hub or pall built into the motor 44.

As the shaft 78 rotates to open the valve 10, rotary motion is transmitted through the electrically operable clutch 76 to the screw 62. The screw 62 is rotated so as to cause the clamp bar assembly 24 to move in the direction of the arrow 66 thereby unclamping the tubing T. This process also winds the spring 40 to provide energy to subsequently close the valve 10. The motor 44, the clutch 76 and the screw 62 cooperate to move the assembly 24 to the open position in opposition to the closing force exterted by the spring 40.

Once the motor 44 has rotated the screw 62 so that the clamping bar 26 no longer closes the tubing T, the electrical power may be removed from the motor 44. The pall or hub in the motor 44 restrains the output shaft 78 of the motor 44 from moving in the reverse direction notwithstanding the continuously applied closing force due to the wound torsion spring 40. Hence, the valve 10 will remain in its open condition and fluids will be permitted to flow through the tubing T even though the motor is not energized provided, however, that the clutch 76 is continuously electrically energized during this time period. This thus results in lower power consumption than that necessary to initially open the valve.

When it is desirable to close the valve 10 and pinch off the tubing T, the clutch 76 is deenergized. The screw 62 can now rotate in the reverse direction due to the force of the torsion spring 40. This reverse rotation of the screw 62 causes the clamp bar assembly 24 to move opposite the direction of the arrow 66 to the closed position thereby closing off the tubing T.

Again with respect to FIG. 2, the motor 44 for example can be a Kingston Model 60-3 high torque synchronous motor with a built-in antirotation gear or hub. Such motors are rated for 55 inch-ounces of starting torque at 9 rpm's rotation and require 3.5 watts of AC power. The clutch 76 can be any conventional electrically operable clutch which can mechanically transmit the torque generated by the motor 44. Such clutches are typically operated with DC currents and voltages requiring on the order of 90 volts DC and 0.05 amps DC to energize or engage the clutch. The process of engaging the clutch transmits mechanical power from the output shaft 78 of the motor 44 to the screw 62. Clutches of the type 76 require on the order of 4½ watts. Hence, the valve 10 of FIG. 2 consumes on the order of 8 watts during the opening phase when the clamp head assembly 24 is moving linearly in the direction of the arrow 66 and about 4½ watts during the time the clamp bar assembly 24 is held in the fully open position.

A thrust bearing assembly 80 is formed out of two washers 82 and one thrust bearing 84 to reduce frictional effects on the screw 62 during the closing phase due to the closing force of the spring 40. The spring 40 is a standard torsion spring that can typically generate 16 inch-ounces of torque. In combination with the screw 62, because of the mechanical advantage which results from using the screw 62, the closing force applied by the clamp bar assembly 24 and the pinching bar 26 to the tubing T nominally is on the order of 20 pounds. This results in a closing force substantially greater than the torque generated by the motor 44. As a result, the valve 10 very abruptly shuts off the flow through the tubing T when power is removed from the clutch 76.

Further with respect to FIG. 2, housing 36 is a molded plastic housing having two parts 36a and 36b which can be screwed together to contain the clutch 76. Both of the nuts 54, 56 can be formed from a polymer, such as a plastic, thereby insulating the clamp bar assembly 24 from the electric motor 44.

FIG. 3 illustrates a side view of the valve 10 with the assembly 24 in the open position linearly extended in the direction 66. As can be seen from FIG. 3, in this condition the tubing T is not pinched shut. Because of the closing forces generated by the torsion spring 40, the tubing T should have a thickness on the order of 25 thousandths of an inch or greater. As can be seen in FIG. 3, the plastic retaining nut 54 in combination with the clamp nut 56 have lifted the switch actuator assembly 64 into an upper position.

FIG. 4 a view taken along line 4—4 of FIG. 3 illustrates the control switch assembly 46 when the switch actuator mechanism 64 is in the upper position shown in FIG. 3. The switch assembly 46 includes three control switches 86, 88 and 90. Control switch 86 is closed, as shown in FIG. 4, when the valve 10 is in its open position as shown in FIG. 3. Switches 86 and 90 sense the condition of the valve 10 when it is closed. Signals from the switches 86, 88, 90 can be used to provide information to related equipment as to the position of the valve 10.

FIG. 5 illustrates the valve 10 in the closed condition when the clamp bar assembly 24 has moved opposite the direction 66, linearly, and the pinch bar 26 has clamped the tube T closed. In the condition shown in FIG. 5, the switch actuator assembly 64 has been moved downwardly by the nuts 54, 56.

FIG. 6 is a view taken along line 6—6 of FIG. 5 illustrating the switch assembly 40 with the switch actuator mechanism 64 in the lower position corresponding to FIG. 5. In this condition the control switch 90 is actuated or closed indicating a closed with tubing present condition. In the event that the tubing T is not present, the switch 88 is also closed by the assembly arm 64 indicating a valve closed without tubing condition.

The switches 86, 88 are adjustably mounted on a movable plate 92 which is slidable on the plate 46 and which can be locked in place by a locking plate 94.

The assembly 48 can include a rectifier to provide DC current for the clutch 76, a connector to connect the valve to an AC supply as well as indicator lights.

FIG. 7 illustrates another embodiment of the present invention. A head support assembly 96 has a centered hexagonal boring 98 therein. A clamp head assembly 100 having an hexagonal cross section is positioned therein. The hexagonal assembly 100 can only move linearly in the boring 98. With the embodiment of FIG. 7, the alignment members 68 of FIG. 2 are not necessary.

Modifications and variations of the present invention are possible in light of the above teaching. For example, the broader aspects of the invention include the use of alternate forms of motors or clutches as well as other arrangements of shafts and couplings. The broader aspects of the invention can also include incorporating a position sensor into the valve and using the valve as a variable position flow control device. It is therefore to be understood that within the scope of the appended claims the invention may be practiced, otherwise than as specifically described.

What is claimed and desired to be secured by Letters Patent of the United States is:

1. A device for occluding fluid flow through a flexible tubing comprising:

a clamping bar linearly moveable from a first position away from a transverse portion of said flexible tubing to allow fluid to flow through said tubing to a second position against said portion of said tubing to prevent fluid flow;

a shaft having a first end and a second end, said first end connected to said clamping bar;

a retaining means having first and a second portions, said first portion in fixed engagement with said second end of said shaft;

a screw having first and second ends, said first end of said screw in threaded engagement with said second portion of said retaining means;

means for preventing rotational movement of said shaft;

an electrically engagable clutch having a hub, said second end of said screw being attached to said hub, rotational motion of said clutch causing rotational motion of said screw and linear motion of said shaft, said retaining means, and said actuator assembly, said clutch maintaining a fixed position as long as said clutch is electrically engaged;

a spring member having a first end fixedly engaged to said hub and a second end located in a fixed position, rotation of said clutch in a first direction causing said spring to tighten and causing said clamping bar to move to said first position and rotation of said clutch in a second direction, opposite said first direction, causing said bar to move to said second position;

an electrically actuatable motor having a shaft restrained to rotate in said first direction only, said shaft being in releasable engagement with said clutch, said motor engaging said clutch when said clutch and said motor are electricaly actuated to rotate said screw in said first direction; and means for independently electrically actuating said shaft in said clutch, said spring member causing said screw and said clutch to rotate in said second direction when said clutch is not electrically engaged.

* * * * *